(12) United States Patent
Barata et al.

(10) Patent No.: US 9,938,313 B2
(45) Date of Patent: Apr. 10, 2018

(54) RECTANGULAR PARALLELEPIPEDAL MALTITOL

(71) Applicant: ROQUETTE FRERES, Lestrem (FR)

(72) Inventors: Manuel Barata, Gonnehem (FR); Pierrick Duflot, La Couture (FR); Abdelfattah Bensouissi, Reims (FR); Mohamed Mathlouthi, Coulommes-la-Montague (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 15/285,057

(22) Filed: Oct. 4, 2016

(65) Prior Publication Data

US 2017/0037073 A1 Feb. 9, 2017

Related U.S. Application Data

(62) Division of application No. 12/333,604, filed on Dec. 12, 2008, now abandoned.

(30) Foreign Application Priority Data

Dec. 12, 2007 (FR) ...................................... 07 59793

(51) Int. Cl.
*C07H 15/04* (2006.01)
*A23L 27/30* (2016.01)

(52) U.S. Cl.
CPC .............. *C07H 15/04* (2013.01); *A23L 27/34* (2016.08); *A23V 2002/00* (2013.01)

(58) Field of Classification Search
CPC ................................ C07H 15/04; A23L 27/34
See application file for complete search history.

(56) References Cited

U.S. PATENT DOCUMENTS

| | | | |
|---|---|---|---|
| 4,408,041 A | 10/1983 | Hirao et al. |
| 4,846,139 A | 7/1989 | Devos et al. |
| 5,580,601 A | 12/1996 | Ribadeau-Dumas et al. |
| 5,583,215 A | 12/1996 | Kawashima et al. |
| 5,597,416 A | 1/1997 | Fuisz et al. |
| 5,651,829 A | 7/1997 | Caboche |
| 2001/0006956 A1 | 7/2001 | Leleu et al. |
| 2006/0078662 A1 | 4/2006 | Staniszewski et al. |

FOREIGN PATENT DOCUMENTS

| | | |
|---|---|---|
| EP | 0735042 | 10/1996 |
| EP | 0741140 | 11/1996 |
| EP | 0905138 | 3/1999 |

OTHER PUBLICATIONS

Fox et al, ed., "Physics and chemistry of the organic solid state", vol. II, 1965, Interscience Publishers, p. 725-767.
Capet et al., Carbohydrate Research, 2004, 339, p. 1225-1231.
Definition of square, Free Merriam-Webster Dictionary, http://www.merriam-webster.com/dictionary/square, accessed online on Aug. 22, 2013.
Davidovich et al., American Pharmaceutical Review, 2004, 7(1), p. 10, 12, 14, 16 and 100.
Ohno et al., "X-Ray Crystal Structure of Maltitol (4-O-X-D-Glucopyranosyl-D-Glucitol)", Carbohydrate Research, 1982, pp. 163-171, vol. 108, Elsevier Scientific Publishing Company, Amsterdam, The Netherlands.
French Patent Office Preliminary Search Report, dated Jul. 25, 2008 and issued in corresponding French Patent Application No. 0759793.

*Primary Examiner* — Jonathan S Lau
(74) *Attorney, Agent, or Firm* — Blank Rome LLP (57) ABSTRACT

The invention concerns maltitol crystals, characterized in that they have a rectangular parallelepipedal shape and have a length to width dimensional ratio in the range 1.8 to 5.3, preferably 3±0.7, and a process for producing them.

7 Claims, 11 Drawing Sheets

RECTANGULAR PARALLELEPIPEDAL MALTITOL

The present invention relates to maltitol crystals of a particular shape and to crystalline compounds containing them. It also relates to a particular process for producing said crystals and compositions.

Maltitol (1,4-O-α-D-glucopyranosyl-D-glucitol) is a polyol obtained by hydrogenating maltose.

The absence of reducing end in the maltitol molecule endows it with great stability, both thermally and chemically.

It has fewer calories than saccharose and its organoleptic properties are close to those of that sugar. It is non-cariogenic and is thus used in many applications, both nutritional and pharmaceutical.

For a long time, maltitol has only been available commercially in the shape of low strength syrups or in the shape of amorphous and impure powders.

It was only at the beginning of the 1980s that the firm HAYASHIBARA described for the first time, in its U.S. Pat. No. 4,408,041, the production of anhydrous maltitol crystals.

Until then, that polyol had always been considered to be a non-crystallizable product.

This erroneous premise had its origins in the fact that crystallizing maltitol from a supersaturated solution is not as easy to control as with other polyols such as mannitol or erythritol, for example.

So-called "mass" techniques on the one hand and water crystallization techniques on the other hand are nowadays almost the only processes which are employed on an industrial scale.

The products obtained thereby, however, exhibit a highly variable degree of crystallinity and not all of them are suitable for specific applications such as chewing gum or chocolate.

Further, such crystalline products are not completely satisfactory when, for example, maltitol is used to substitute saccharose or lactose in dry dosage shapes such as capsules, soluble powder type medication, tablets and powdery nutritive preparations for dissolution.

This is also the case when the same type of substitution is to be made in sweetened foods such as powdered drinks, desserts, cake preparations or chocolate-flavoured or vanilla-flavoured breakfast powders.

For such specific applications, it has been observed, in particular for pseudo-crystalline maltitol powders obtained by the mass technique and to a lesser extent for crystalline maltitol powders obtained by the water crystallization technique, that these have one or more disadvantages, particular examples of which are:

- they do not flow readily;
- they have a tendency to cake or clump;
- they only dissolve very slowly in water;
- they are poor excipients for compression; or
- they do not meet the identification and purity criteria set by various pharmacopoeias.

Specialists in the field of polyol crystallization have thus set themselves the task of developing maltitol compositions which do not suffer from the disadvantages associated with flow, clumping, dissolution, or compression which known maltitol powders have.

Of course, it might be thought that the identified need could be met by using other polyols. However, this is demonstrably impossible, since none of them has the characteristics of solubility, hygroscopy, sweetened flavour and fusion properties as close as those of saccharose as maltitol.

However, as can readily be deduced from an analysis of the various contributions made by the prior art, very little of the work which has been undertaken has been concerned with the influence that the shape of the maltitol crystals may have in overcoming the disadvantages cited above.

The corollary is that very little work has been concerned with determining what crystallization conditions could be employed to encourage the production of a particular shape of maltitol crystals.

In U.S. Pat. No. 4,408,041, for example, in order to be able to crystallize maltitol, HAYASHIBARA only recommends to start from a maltitol syrup having a high maltitol content and as a result, contains a small quantity of polyols with a higher DP (DP3 and DP being 4 or more).

It will be observed therein that the crystals obtained are only presented as "colourless, odourless and transparent".

Figure 2:
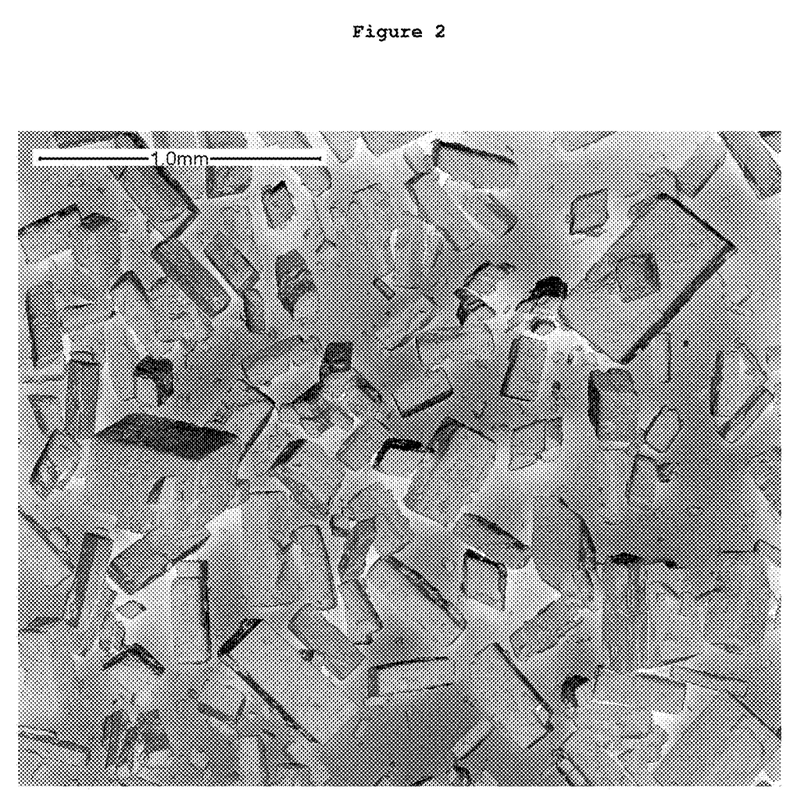
FIGS. 2 to 5 illustrate crystals with a rectangular parallelepipedal shape from a first batch of crystals in accordance with the invention. The photographs were recorded from the microscope using the following magnifications: 50 times (FIG. 2), 100 times (FIG. 3), and 200 times (FIGS. 4 and 5).
Figure 3:
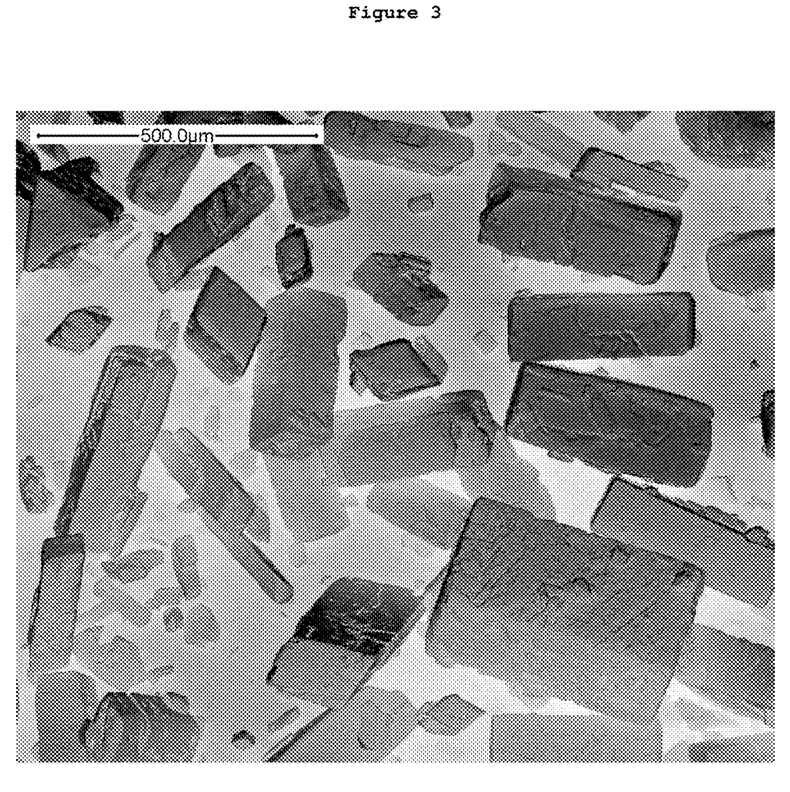
Figure 4:
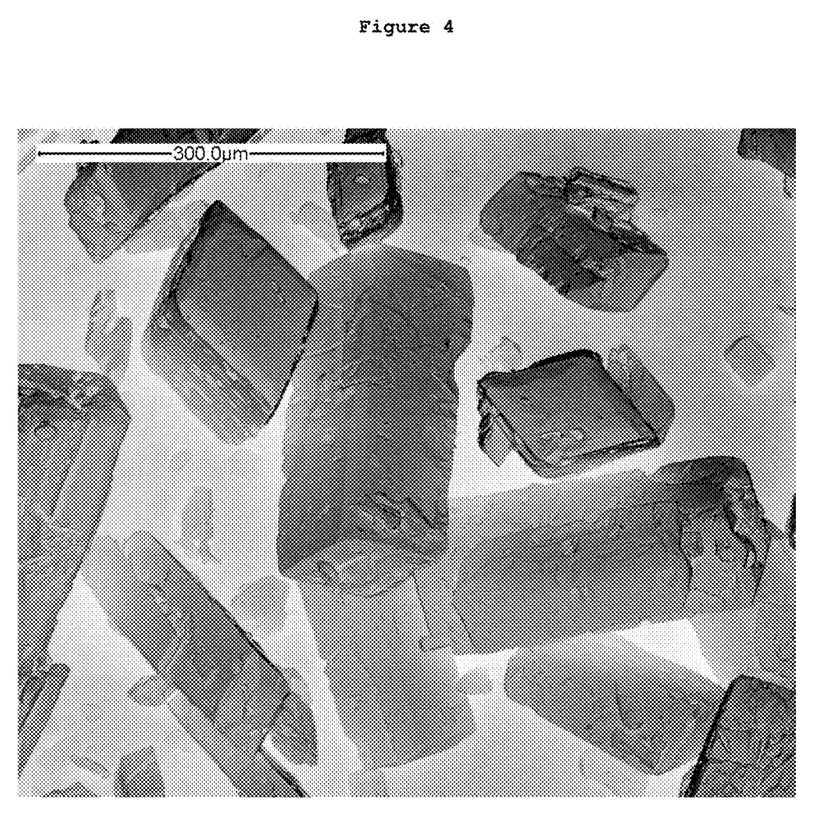
Figure 5:
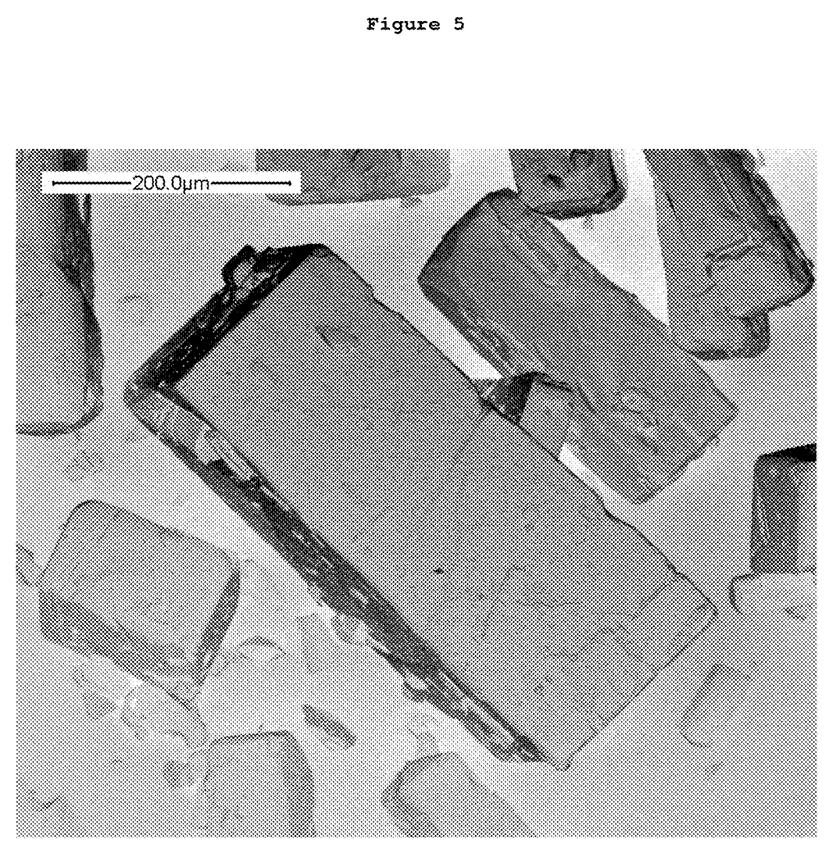
Figure 6:
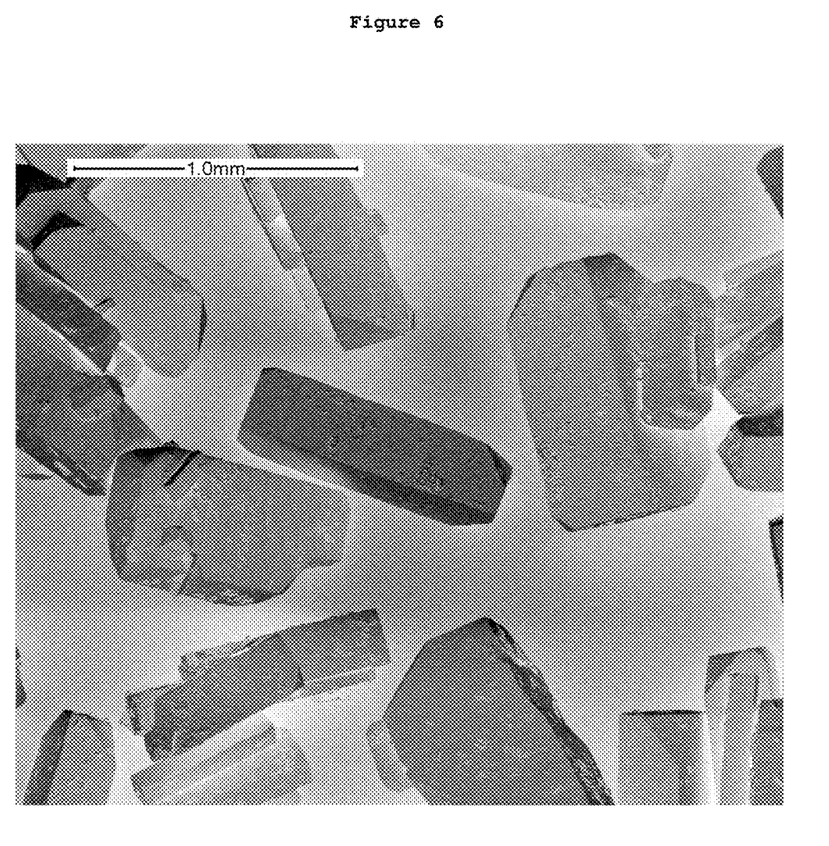
FIGS. 6 to 10 illustrate crystals with a rectangular parallelepipedal shape from a second batch of crystals in accordance with the invention. The photographs were recorded from the microscope using the following magnifications: 50 times (FIGS. 6 and 10), 100 times (FIGS. 7 and 8), and 200 times (FIG. 9).
Figure 7:
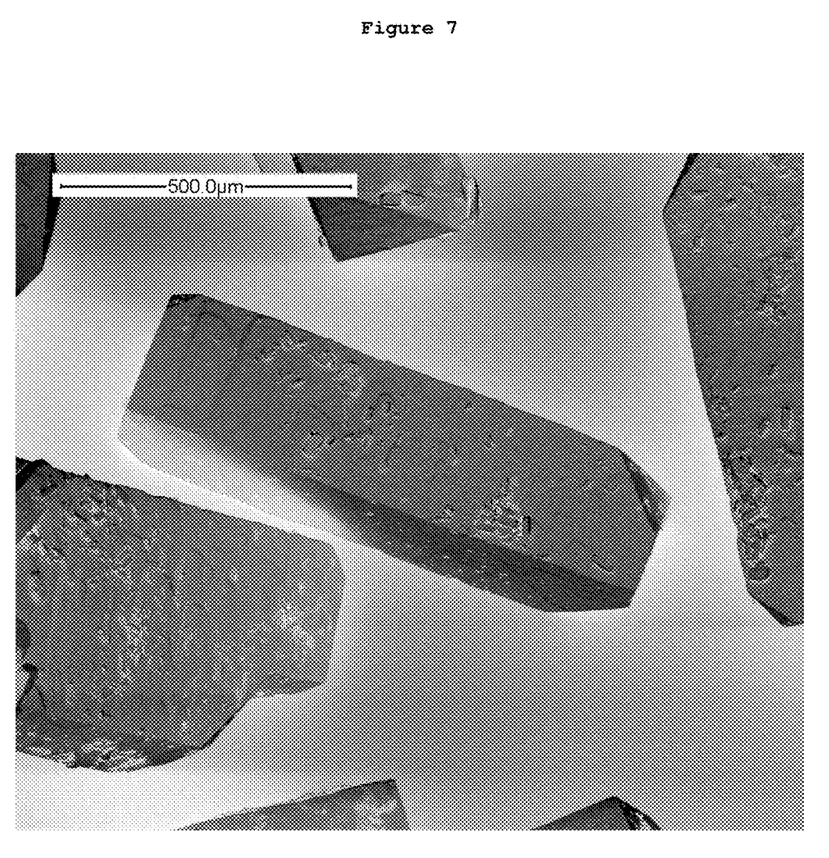
Figure 8:
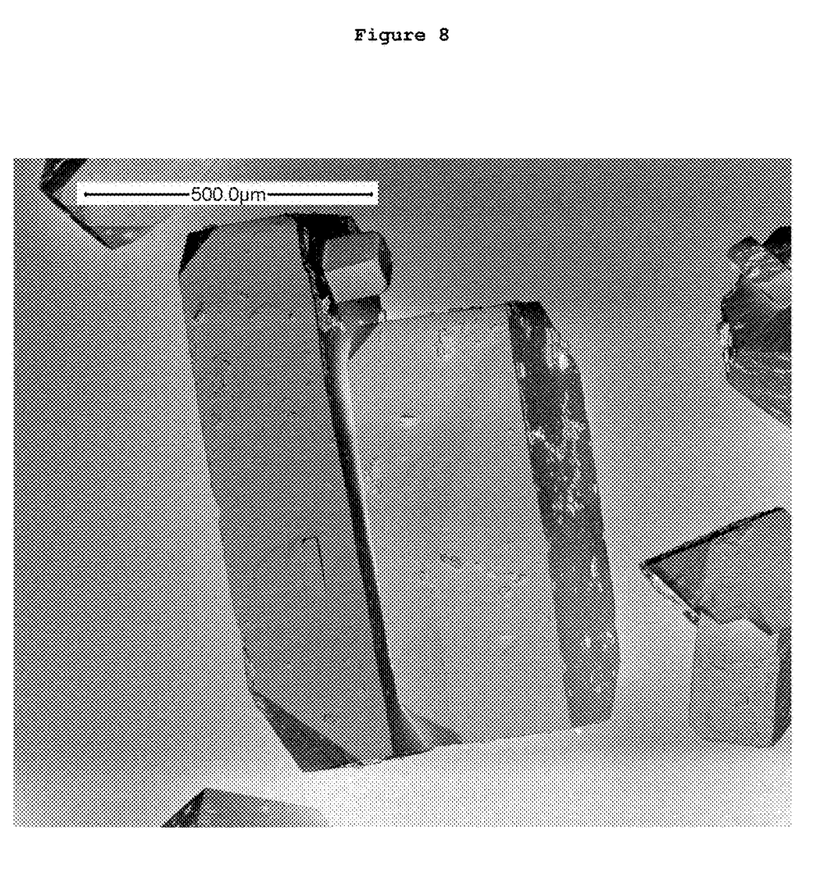
Figure 9:
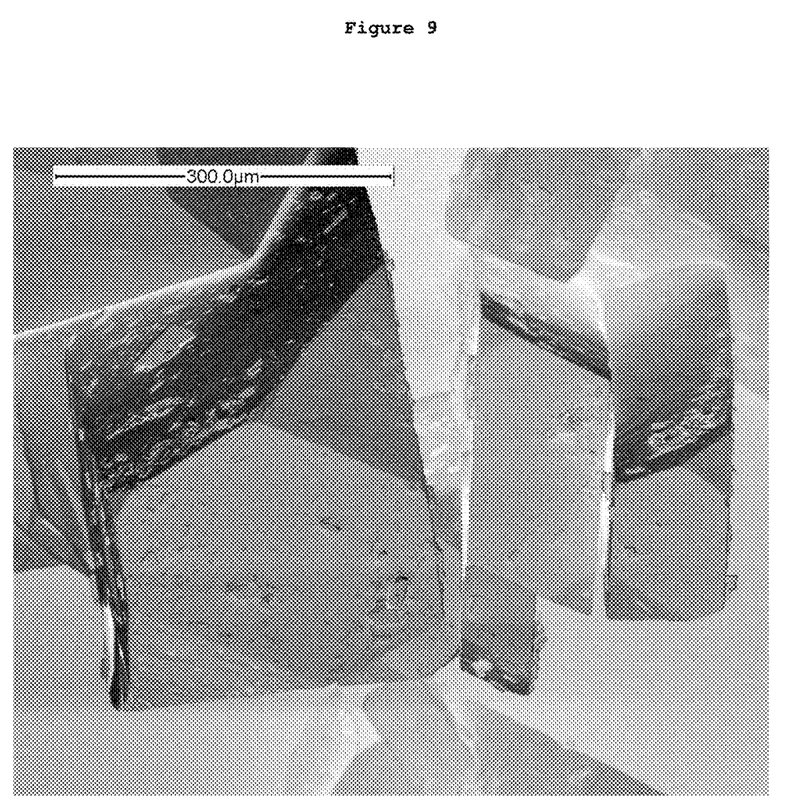

The crystals obtained are described by way of electron microscope photos (FIG. 3 is an overview of said crystals (magnification stated to be ×150) and FIG. 4 is taken at a greater magnification (×600), but it will be observed that HAYASHIBARA does not comment on them.

FIG. 4 allows the skilled person to observe that the maltitol crystals obtained have a "parallelepipedal—somewhat cubic" shape.

In 1982, in its scientific article published in Carbohydrate Research regarding the X-ray crystallographic analysis of maltitol, HAYASHIBARA would have been expected to describe the crystals in a little more detail.

However, OHNO et al. described them succinctly as "colourless and prism-like" and did not associate that crystalline shape with any functional property of the maltitol.

In fact, the crystal observed in that article was a "macrocrystal" which had been specially manufactured in order to be able to determine the lattice parameters of the crystal by X-ray diffraction.

The crystal was a "cubic prism" since the authors stated that the dimensions were 0.3×0.3×0.3 mm.

In 1989, the Applicant, in U.S. Pat. No. 4,846,139, itself also described a process for preparing crystalline maltitol.

Crystallization was carried out in water. However, the discussion did not focus on the crystals and no particular shape was remarked upon.

U.S. Pat. No. 5,583,215 granted to TOWA describes a solid crystalline mixture containing maltitol. The starting maltitol solution which is crystallized contains 80% to 98% of maltitol, 0.5% to 15% of sorbitol and 1.5% to 10% of maltotriitol, and DP≥3.

Crystallization is carried out by extrusion.

The only mention of the "aspect" of the mixture of crystals obtained is that of a "crushed and relatively tight" structure, but a particular shape of the crystals is neither noted nor discussed.

It was in another contribution from the Applicant that the influence of the size and shape of the crystals was recognized as being important in certain food applications, and in particular in making confectionery with maltitol.

In U.S. Pat. No. 5,580,601, the Applicant describes the use of xylitol and maltitol crystals for grainy confectionery.

For the maltitol intended for that application, four qualities of maltitol from that time were compared:

MALTISORB® P90 and MALTISORB® P200, sold by the Applicant;

maltitol sold by TOWA under the trade name AMALTY® MR100;

maltitol manufactured as described in Example 2 of U.S. Pat. No. 4,408,041 from HAYASHIBARA.

In U.S. Pat. No. 5,580,601, the Applicant remarks that the four varieties of maltitol were in two different crystalline shapes: an needle-like shape and a parallelepipedal, somewhat cubic shape (that having been presented by HAYASHIBARA in its U.S. Pat. No. 4,408,041).

In U.S. Pat. No. 5,580,601, the Applicant confirmed that during the crystallization process used in accordance with Example 2 of U.S. Pat. No. 4,408,041 from HAYASHIBARA, the maltitol syrup could produce crystals of the "parallelepipedal, somewhat cubic" shape.

Further, it is also stated that finely ground needle-like MALTISORB® P90 powder produces parallelepipedal, somewhat cubic crystals.

Finally, in U.S. Pat. No. 5,580,601, the Applicant discusses the influence of size and shape of the maltitol crystals on the textural quality and stability over time of grainy confectionery which has been so prepared.

Thus, it is concluded that:

it is only possible to prepare grainy maltitol confectionery which is of excellent textural quality and is particularly stable over time when it contains 50% to 93% maltitol with respect to the total amount of sweetener, and then only if the maltitol which is present at least partially in the crystallized in the confectionery is essentially present in the shape of crystals with a dimension of less than 60 microns, preferably less than 40 microns and more preferably less than 20 microns;

if the crystals contained in the confectionery are needle-like, i.e. have a length of approximately 120 microns and a section of approximately 35 microns, for example, then the confectionery tends to change rapidly and harden excessively. This is not the case when it contains crystals which are preferably parallelepipedal, somewhat cubic with a dimension of less than 60 microns. In this case, the grainy confectionery is stable for several months. The crystals thus have a high maltitol purity exceeding 95% and usually 98%, or even 99%.

In its patent EP-735 042, the Applicant describes a novel crystalline maltitol composition. This time, crystallization is achieved by spray drying.

The crystals obtained are described as being of an essentially porous and alveolar structure, in the shape of essentially spherical particles which are free of sharp edges and composed of a multitude of crystalline microparticles which are agglomerated together.

The observed structure differs clearly from that of a maltitol crystallized from water and an extruded maltitol, constituted by parallelepipedal, somewhat cubic particles.

In another patent, EP-741 140, TOWA describes a process for preparing crystalline maltitol, and a solid crystalline mixture of crystallized maltitol. In this case, crystallization is carried out in water.

However, no inshapeation is provided regarding the shape of the crystals.

Things had to wait until the Applicant filed patent EP-905 138 for another major advance to be made.

In that patent, the Applicant developed maltitol compositions which did not suffer from any disadvantages as regards flow, clumping, dissolution, or compression that known maltitol powders exhibited.

While working on developing those maltitol compositions, the Applicant was able to isolate two particular shapes of maltitol crystals other than the needle-like shape and the parallelepipedal, somewhat cubic shape: the bipyramidal shape and the prismatic shape.

At the time, the Applicant explained the existence of those two shapes of maltitol crystals by the maltotriitol content in the maltitol syrup to be crystallized.

The Applicant observed that by controlling the quantity of maltotriitol in a maltitol syrup, it was possible to orientate the shape of the maltitol crystals towards one or other of the shapes or towards a mixture of the two shapes when that maltitol syrup underwent a crystallization step.

In its patent EP-905 138, the Applicant made a point of observing that the crystallization shapes (bipyramidal or prismatic) necessarily had important consequences both regarding manufacture and applications.

Thus, a semi-crystallized mass of maltitol comprising a certain percentage of prismatic crystals is more viscous than a mass comprising the same percentage of bipyramidal crystals, all other things being equal, in particular when considering the large crystal size.

Thus, to prepare spray dried maltitol, it is preferable to select suspensions containing very few maltotriitol and further containing bipyramidal crystals rather than prismatic crystals to avoid caking.

In other aspects, the use of bipyramidal maltitol crystals appears to be advantageous for producing chocolate (more thickened mass before refining), chewing gums (possibility of retaining a flexible texture with a large quantity of powdery maltitol), dry dosage shapes (better flow), etc.

In contrast, a prismatic shape is more compressible and allows caking (mass increase) with a low crystal content, as sometimes required (chewing gums, chewing gum cores to be sugar-coated).

BRIEF DESCRIPTION OF THE DRAWINGS

FIG. 1 illustrates scanning electron microscope photographic images of four crystalline shapes: parallelpipedal, prismatic, bipyramidal, and needle-like, respectively 1.1, 1.2, 1.3 and 1.4.

DETAILED DESCRIPTION OF THE INVENTION

It is apparent from the foregoing that it is important to select particular dimensions and shapes for the maltitol crystals when used in specific way considering the application field.

Thus, four crystalline shapes have been documented:
the parallelepipedal, somewhat cubic shape;
the prismatic shape;
the bipyramidal shape; and
the needle-like shape.

FIG. 1 illustrates these four crystalline shapes (respectively 1.1, 1.2, 1.3 and 1.4) (scanning electron microscope photographic images under the conditions defined below).

While carrying out research on the crystallization of maltitol, the Applicant discovered, completely unexpectedly, that maltitol could crystallize in a fifth crystalline shape which is completely different from the shapes described above, opening up other applications for crystalline maltitol: the rectangular parallelepipedal shape.

Within the context of the invention, the term "rectangular parallelepipedal" shape means a polyhedron wherein at least four of its six faces are rectangles.

The observations were made using an FEI, QUANTA 200 FEG model, scanning electron microscope.

The crystals were observed at a tension of 1 keV.

Thus, in a first aspect the invention concerns crystals with a rectangular parallelepipedal shape illustrated in FIGS. 2 to 9.

These crystals are not agglomerated or organized into small agglutinated packs but, on the contrary, are well dissociated and individualized from each other.

The photographs were recorded from the microscope using the following magnifications:
  50 times (FIG. 2), 100 times (FIG. 3), 200 times (FIGS. 4 and 5) for observation of a first batch of crystals in accordance with the invention;
  50 times (FIGS. 6 and 10), 100 times (FIGS. 7 and 8) and 200 times (FIG. 9) for observation of a second batch of crystals in accordance with the invention.

The figures clearly illustrate the fact that the maltitol crystals are rectangular parallelepipedal in shape in the context of the invention.

Figure 11:
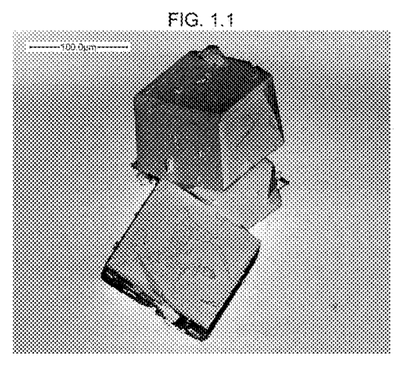
FIG. 11 illustrates a diagram of a rectangular parallelepiped.
Figure 12:
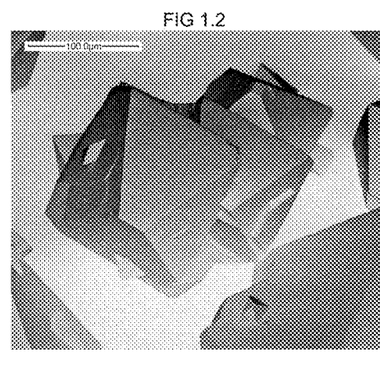
Figure 13:
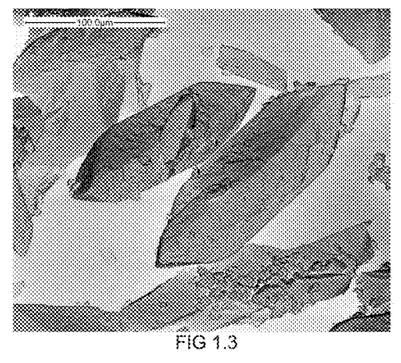
Figure 14:
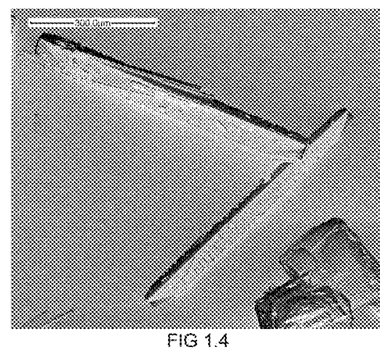

In considering the diagram shown in FIG. 11, taking the largest surface as the base (defined by points AEHD or BFGC), it can be seen that the lateral faces (ABFE and DCGH) are parallelograms the angle α between the lateral edge and the base plane being variable, and in which the other faces are rectangular parallelograms.

In this case, the rectangular parallelepiped is defined by 4 dimensions, the length (here AD), the width (AE) and the height (AB) as well as the value of the angle α.

In accordance with the invention, the angle α is from 90° to 50°.

Two populations of rectangular parallelepipedal crystals are thus observed, populations which can co-exist in all proportions in the same composition within the invention:
  maltitol crystals, characterized in that the two smallest faces of the rectangular parallelepiped (the faces defined as ABFE and DCGH in the diagram above) are parallelograms with substantially equal sides;
  In this case, the crystal shape is that of a polyhedron wherein four of its six faces are rectangles, the two others possibly being lozenge (where the value of angle α can be from 50° to 90°, preferably in the range 60° to 70°) or squares (the angle α being 90°);
  other maltitol crystals, characterized in that the two smallest faces are parallelograms with paired equal sides (angle α being 90°);
  In this case, the crystal shape is that of a polyhedron with four faces which are rectangles; the two others are also rectangular parallelograms. In this case, the skilled person obtains a geometric shape which is designated as rectangular parallelepiped.

FIGS. 6 to 9 show maltitol crystals in accordance with the invention, characterized in that the two smallest faces of the rectangular parallelepiped are parallelograms whereof at least one angle comprises a truncation.

The maltitol crystals of the invention are characterized in that the ratio of the length (dimension AE in the diagram above) to the width (dimension AB in the diagram above) of the rectangular parallelepiped is in the range 1.8 to 5.3, preferably in the range 2.3 to 3.7.

Figure 10:
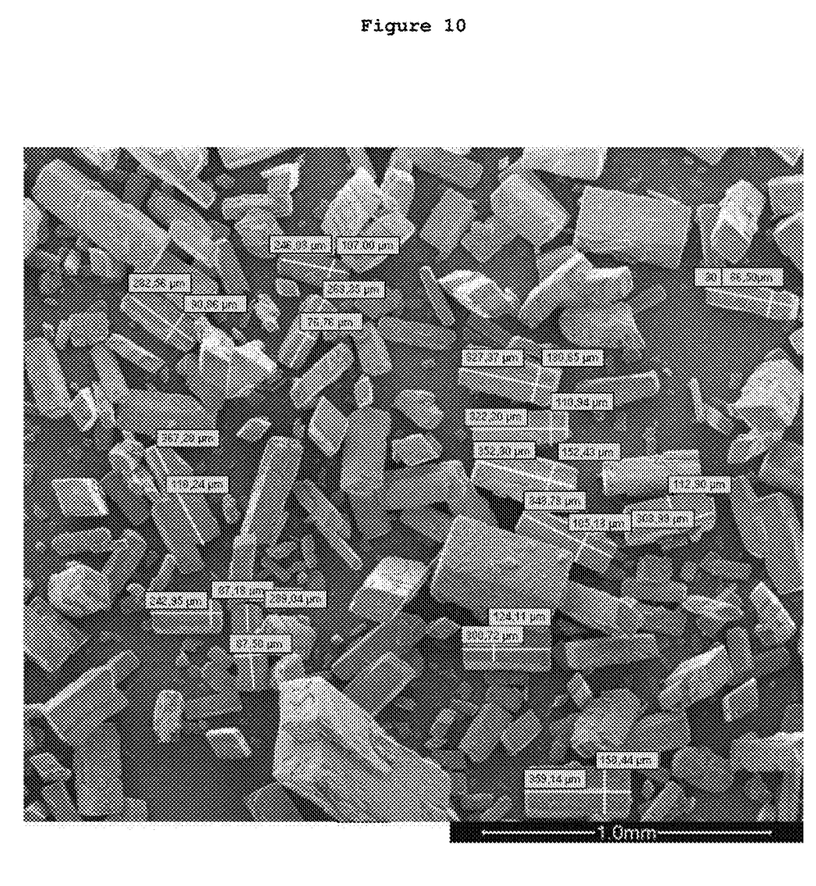

This value was determined by measuring the dimensional ratio of about thirty individualized crystals as shown in FIG. 10 (showing and quantifying the dimensions of several crystals).

The values were obtained by determining the width and length of the rectangular faces of each of the rectangular parallelepipeds observed.

The maltitol crystals of the invention are also characterized in that the length of the rectangular parallelepiped (dimension AD in the diagram above) is in the range 50 to 750 μm, preferably in the range 97 to 280 μm.

To allow identification of the crystalline shapes, a reflection X-ray diffraction technique was used on maltitol crystals powder employing test A below.

Test A consists of determining the relative intensities of diffraction peaks. Diffraction spectra are obtained with a powder analysing X-ray diffractometer provided with a cobalt source. The analysis is carried out by reflection with a rotating sample holder. The sample is compacted manually into the sample holder. The analysis is carried out continuously from 4° to 34°. The intensities of the peaks are measured and normalized with respect to the most intense peak of the diffraction spectrum.

The maltitol crystals of the invention are thus characterized in that X-ray diffraction profile, determined using the test A, has an intensity of 100% for the peak at 26.51°, and an intensity of 0% for the peak at 16.07°.

As will be shown in the comparative example given below, the maltitol crystals of the invention have a profile which is unique compared with the four other known crystalline shapes of maltitol.

Maltitol with the bipyramidal shape and that with the cubic parallelepipedal shape provide the following:
  an intensity in the range 0 to 0.15% for the peak at 16.07°;
  and are characterized by the intensity of their peak at 26.51°:
    between 54.46% and 81.76% for the cubic parallelepipedal shape;
    between 60.1% and 73.7% for the bipyramidal shape.

Regarding maltitol with the prismatic shape and that with the needle-like shape, they provide an intensity of 100% for the peak at 26.51°, but for the peak at 16.07°:
  an intensity in the range 0.14% to 0.26% for the prismatic shape; and
  an intensity in the range 0.33% to 0.42% for the needle-like shape.

The invention also concerns a crystalline maltitol composition, characterized in that it is wholly or partially constituted by crystals with a rectangular parallelepipedal shape.

This crystalline maltitol composition is in particular characterized in that the crystalline fraction of the maltitol is constituted by at least 50% by weight of crystals with a rectangular parallelepipedal shape, preferably 70% to 100% by weight, more preferably 95% to 100%.

In order to prepare the maltitol syrup which, after crystallization, can produce the crystalline shapes of maltitol of the invention, the process described below or an equivalent process is implemented.

The first step of the process is known per se. It consists of liquefying a starch milk which may be of any botanical origin: it may derive from wheat, corn or from potato, for example.

This starch milk is supplemented with acid in the case of "acid" liquefaction, or with an α-amylase in the case of enzymatic liquefaction.

In the process of the invention, it is preferable to carry out controlled hydrolysis of the starch milk to obtain a liquefied starch milk with a low degree of transshapeation. Thus, the temperature, pH, enzyme content and calcium content conditions, which are known to the skilled person, are determined such that they can produce a DE (dextrose equivalent) of less than 10, preferably less than 6, and more particularly less than 4.

Preferably, the liquefaction step is carried out in two sub-steps, the first consisting of heating, for several minutes and at a temperature in the range 105° C. to 108° C., the starch milk in the presence of an α-amylase (type TERMAMYL® 120L sold by NOVOZYMES) and a calcium-based activator, the second consisting of heating the treated starch milk to a temperature in the range 95° C. to 100° C. for one to two hours.

Once the liquefaction step is complete, using dry matter content, pH, enzyme content and calcium content conditions which are well known to the skilled person, the α-amylase is then inhibited. This α-amylase inhibition may preferably be carried out thermally by implementing, following liquefaction, a thermal shock for a few seconds at a temperature of 130° C. or more.

The saccharification step is then carried out. During this step, the liquefied starch milk is subjected to the action of a maltogenic α-amylase such as that sold by NOVO under the trade name MALTOGENASE®. During this first saccharification step, the maltogenic α-amylase may be added all at once or in several doses.

Next, after allowing the maltogenic α-amylase to act, saccharification of the liquefied starch milk can be continued using a β-amylase such as that sold by GENENCOR under the trade name SPEZYME® BBA 1500.

During these steps, it suffices to combine an enzyme which specifically hydrolyses the alpha-1,6 bonds of the starch with the enzymes having a maltogenic activity (maltogenic α-amylase and β-amylase). This addition of a debranching enzyme can on the one hand accelerate the hydrolysis reactions without simultaneously accelerating the reversion reactions, and can also reduce the quantity of highly branched oligosaccharides which normally resist the action of maltogenic enzymes.

This addition of a debranching enzyme may be carried out on adding the maltogenic α-amylase or on adding the β-amylase.

This debranching enzyme is selected from the group constituted by pullulanases and isoamylases.

The pullulanase is, for example, that sold by ABM under the trade name PULLUZYME®.

The isoamylase is, for example, that sold by HAYASHIBARA.

The saccharification step may also be carried out entirely or partially in the presence of fungal α-amylase.

When saccharification is complete, it is possible to add a little α-amylase, which generally improves the subsequent filtration steps. The quantities and conditions for action of the various enzymes employed in the steps for liquefaction and saccharification of the starch milk are generally those which are recommended for the hydrolysis of starch and are well known to the skilled person.

Saccharification is carried out until the maltose hydrolysate contains at least 85% by weight of maltose (dry/dry).

The saccharified hydrolysate is then filtered on a pre-coated filter or by micro-filtration membrane, then demineralized.

The maltose hydrolysate obtained may then readily be catalytically hydrogenated.

Hydrogenation of such a hydrolysate is carried out in accordance with standard procedures which, for example, result in the production of sorbitol from glucose.

For this step, it is possible to use both catalysts based on ruthenium and RANEY nickel catalysts. However, it is preferable to use RANEY nickel catalysts which are cheaper.

In practice, 1% to 10% by weight of catalyst is used with respect to the dry matter content of the hydrolysate which undergoes hydrogenation. Hydrogenation is preferably carried out on a hydrolysate with a dry matter content in the range 15% to 50%, but in practice rather in the range 30% to 45%, at a hydrogen pressure in the range 20 to 200 bar. It may be carried out continuously or discontinuously.

When operating discontinuously, the pressure of the hydrogen used is generally in the range 30 to 60 bar and the temperature at which hydrogenation is carried out is in the range 100° C. to 150° C. Care is taken to maintain the pH of the hydrogenation medium by adding sodium hydroxide or sodium carbonate, for example, but without exceeding a pH of 9.0. This protocol can avoid the formation of cracking or isomerization products.

The reaction is stopped when the amount of reducing sugars in the reaction medium drops below 1%, preferably below 0.5% and more particularly below 0.1% (dry/dry).

After cooling the reaction medium, the catalyst is eliminated by filtration and the maltitol syrup obtained is demineralized on cationic and anionic resins. At this stage, the syrups contain at least 80% maltitol (dry/dry).

To obtain the crystalline shapes of maltitol in accordance with the invention, the Applicant has discovered that crystallization of the maltitol syrup must be carried out under particular conditions.

The skilled person will be well aware that the final shape of a crystal is largely dependent on the crystallization conditions.

Impurities also modify the shape (or habitus) of the crystal, such as the prismatic and bipyramidal shapes of the maltitol crystal which are obtained in the presence of different concentrations of maltotriitol, as described above (in accordance with the disclosure in patent EP-905 138).

The Applicant has thus discovered, and this constitutes one of the essential characteristics of the process of the invention, that the crystalline shape of maltitol can be orientated towards the rectangular parallelepipedal shape by crystallizing maltitol syrup in the presence of aldehydes and condensed dicarbonyl compounds.

These latter are obtained in particular by an intense heat treatment, i.e. at more than 100° C., of glucidic solutions of saccharose, fructose, invert sugars, or glucose syrup type.

The Applicant has discovered that the quantity of impurities must be less than 5%, preferably in the range 1.5% to 4.5%, and more preferably in the range 2.5% to 3.5%.

A preferred embodiment of the process of the invention consists in:

a) preparing a first maltitol syrup with a dry matter content of at least 60% by weight and with a maltitol content of at least 85% by weight;

b) introducing into said maltitol syrup a sugar selected from the group constituting of saccharose, fructose, invert sugars, and glucose syrups, used alone or as a mixture;

c) heating said first maltitol syrup in order to generate impurities constituted by aldehydes and condensed dicarbonyl compounds;

d) preparing a second maltitol syrup with a dry matter content of at least 65% by weight and with a maltitol content of at least 90% by weight;

e) incorporating said second maltitol syrup into the first maltitol syrup in order to obtain a maltitol syrup with a dry matter content of at least 70% by weight and with a maltitol content of at least 80% by weight;

f) concentrating the maltitol syrup obtained to a dry matter content of at least 80%;

g) crystallizing the concentrated maltitol syrup by evaporation and/or cooling;

h) recovering the crystals thereby obtained.

The invention will be better understood from the following examples which are to be construed as being illustrative and non-limiting.

Example 1

A maltitol syrup was prepared into which fructose was introduced such that it had the following composition (syrup A), its dry matter content being 60%:
- 88% over dry matter maltitol;
- 4% over dry matter sorbitol;
- 2% over dry matter with hydrogenated DP≥3;
- 1% of cracking product;
- 5% over dry matter fructose.

It was heated at atmospheric pressure at 120° C. for 2 hours.

A maltitol syrup (syrup B) was obtained with a dry matter content of 75%:
- 37% over dry matter maltitol;
- 19% over dry matter sorbitol;
- 37% over dry matter with DP≥3;
- 7% of cracking product essentially comprising aldehydes and condensed dicarbonyl compounds derived from caramelization.

A maltitol syrup (syrup C) was also prepared having, for a dry matter content of 67%:
- 93% over dry matter maltitol;
- 3% over dry matter sorbitol;
- 2% over dry matter with DP≥3;
- 2% of cracking product.

Incorporation of syrup C into syrup B in a proportion of the order of 3.7 to 1 resulted in a maltitol syrup (syrup D) which contained the following, for a dry matter content of 70%:
- 81.1% over dry matter maltitol;
- 6.4% over dry matter sorbitol;
- 9.4% over dry matter with DP≥3;
- 3.1% of cracking product.

Said syrup D was concentrated to 84% dry matter content by vapour evacuation.

This concentrated syrup was brought to 70° C. then seeded with 0.05% dry matter maltitol crystals ground to 35 μm.

It was cooled by increasing the vacuum in the range 28 to 11 kPa to adjust the temperature from 70° C. to 50° C. over 2 hours, recycling the vapour.

A second crystallization step was carried out by cooling, to increase the crystallization yield and to increase the crystal size, transferring all of the crystalline mass obtained in the preceding step to a double jacket reactor then cooling from 50° C. to 45° C. over 5 hours.

Mother liquors were thus obtained having, for a dry matter content of 72%:
- 68% over dry matter maltitol;
- 12% over dry matter sorbitol;
- 17% over dry matter with DP≥3;
- 3% of cracking product.

The crystalline composition obtained contained 97.6% over dry matter maltitol, 0.2% over dry matter sorbitol and 2.2% over dry matter with DP≥3.

All of the crystalline shapes were primarily of the rectangular parallelepipedal type as shown in FIGS. 2 to 5.

Example 2

Crystallization of syrup D of Example 1 (84% dry matter content) was carried out in an evapocrystallizer cooled by adiabatic evaporation.

The vapours were condensed continuously and re-incorporated.

The residence time was 5 hours, which meant that the temperature of syrup D, initially fixed at 70° C., could be reduced as described in Example 1 to a temperature of 50° C.

The massecuite was then cooled from a temperature of 50° C. to 43° C. over 15 hours in a continuous crystallizer.

A mother liquor was obtained which, for a dry matter content of 72%, had a composition of:
- 65% over dry matter maltitol;
- 13% over dry matter sorbitol;
- 18% over dry matter with hydrogenated DP≥3;
- 4% of cracking products.

The crystalline composition obtained contained 98.1% over dry matter of maltitol, 0.1% over dry matter of sorbitol and 2.3% over dry matter of hydrogenated DP≥3.

These crystallization conditions meant that crystalline shapes could be obtained which were mainly of the rectangular parallelepipedal type, as shown in FIGS. 2 to 5.

Example 3

Crystallization of maltitol syrup D of Example 1 was carried out by cooling in two steps.

The first step was a so-called evaporation phase. It involved concentrating the syrup to obtain a solution with a degree of super-saturation in the range 1.05 to 1.07.

The quantity of water to be evaporated was determined by calculation from the initial concentration.

When the desired super-saturation had been reached, seeding was carried out to introduce a calibrated quantity of 35 μm seed.

The period following said seeding was composed of several cooling phases, as detailed in Table I below.

TABLE I

| | Temperature ramp-up | Temperature variation | Period | Rate used | Mean rate |
|---|---|---|---|---|---|
| STEP 1 | 80 to 64° C. | 16° C. | 48 h | 2° C./6 h | 0.33° C./h |
| STEP 2 | 64 to 52° C. | 12° C. | 18 h | 2° C./3 h | 0.66° C./h |
| STEP 3 | 52 to 46° C. | 6° C. | 3 h | 2° C./1 h | 2° C./h |
| Total: | 80 to 46° C. | 55° C. | 80 h | 0.68° C./h | 0.68° C./h |

A mother liquor was obtained which, for a dry matter content of 72%, had a composition of:
- 67% over dry matter maltitol;
- 10% over dry matter sorbitol;
- 21% over dry matter with hydrogenated DP≥3;
- 2% of cracking products.

All of the crystalline shapes obtained were mainly of the rectangular parallelepipedal type as illustrated in FIGS. 6 to 9, i.e. more particularly, with respect to the shapes obtained in the context of Example 1 and illustrated in FIGS. 2 to 5, having truncations at their two smallest faces.

Without wishing to be bound by a particular theory, the Applicant attributes the observed formation of said truncations on the smallest faces of the rectangular parallelepipedal shapes of the invention to the crystallization kinetics described in this example.

Example 4

Table II below presents the characterization by X-ray diffraction using test A of maltitol crystals of the invention and maltitol powders with different crystalline shapes (corresponding to the crystals of FIG. 1).

TABLE II

| | Rectangular parallelepipedal shape In accordance with the invention | | | Parallelepipedal, somewhat cubic shape | | | Bipyramidal shape | | | Prismatic shape | | | Needle-like shape | | |
|---|---|---|---|---|---|---|---|---|---|---|---|---|---|---|---|
| Intensity of peak at 16.07° (%) | 0 | 0 | 0 | 0 | 0 | 0 | 0.14 | 0 | 0.1 | 0.26 | 0.21 | 0.14 | 0.42 | 0.42 | 0.33 |
| Intensity of peak at 26.51° (%) | 100 | 100 | 100 | 54.46 | 60.87 | 81.76 | 67.3 | 60.1 | 73.7 | 100 | 100 | 100 | 100 | 100 | 100 |

The intensities of the peaks at 16.07° and 26.51° allow the five crystalline shapes of crystalline maltitol to be identified and differentiated.

The invention claimed is:

1. A process for preparing maltitol crystals having a rectangular parallelepipedal shape and a ratio of length to width dimensions being in the range 1.8 to 5.3, wherein a maltitol syrup is crystallized in water in the presence of impurities constituted by aldehydes and condensed dicarbonyl compounds, and maltitol crystals recovered have rectangular parallelepipedal shape and a ratio of length to width dimensions being in the range 1.8 to 5.3.

2. The process according to claim 1, wherein the maltitol crystals have a ratio of length to width dimensions is in the range of 2.3 to 3.7.

3. The process according to claim 1, wherein the impurities are present in a quantity less than 5% (dry/dry).

4. The process according to claim 3, wherein the impurities are present in a quantity in the range 1.5% to 4.5% (dry/dry).

5. The process according to claim 4, wherein the impurities the impurities are present in a quantity in the range 2.5% (dry/dry).

6. The process according to claim 1, wherein the aldehydes and the condensed dicarbonyl compounds are obtained by a heat treatment at more than 100° C. of glucidic solutions selected from the group consisting of saccharose, fructose, invert sugars and glucose syrups.

7. The process according to claim 1, wherein the process comprises:
a) preparing a first maltitol syrup with a dry matter content of at least 60% by weight and with a maltitol content of at least 85% by weight;
b) introducing into said maltitol syrup a sugar selected from the group constituting of saccharose, fructose, invert sugars, and glucose syrups, used alone or as a mixture;
c) heating said first maltitol syrup in order to generate impurities constituted by aldehydes and condensed dicarbonyl compounds;
d) preparing a second maltitol syrup with a dry matter content of at least 65% by weight and with a maltitol content of at least 90% by weight;
e) incorporating said second maltitol syrup into the first maltitol syrup in order to obtain a maltitol syrup with a dry matter content of at least 70% by weight and with a maltitol content of at least 80% by weight;
f) concentrating the maltitol syrup obtained to a dry matter content of at least 80%;
g) crystallizing the concentrated maltitol syrup by evaporation and/or cooling;
h) recovering the crystals thereby obtained.

* * * * *